(12) United States Patent
Hölzer

(10) Patent No.: US 7,241,888 B2
(45) Date of Patent: Jul. 10, 2007

(54) PROCESS FOR PREPARING 10α-[4'-(S,S-DIOXOTHIOMORPHOLIN-1'-YL)]-10-DEOXO-10-DIHYDROARTEMISININ

(75) Inventor: Bettina Hölzer, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 11/145,840

(22) Filed: Jun. 6, 2005

(65) Prior Publication Data

US 2005/0282804 A1 Dec. 22, 2005

(30) Foreign Application Priority Data

Jun. 8, 2004 (DE) .................. 10 2004 027 871

(51) Int. Cl.
*C07D 279/10* (2006.01)
(52) U.S. Cl. ................................. 544/58.2
(58) Field of Classification Search ............. 544/58.2
See application file for complete search history.

(56) References Cited

U.S. PATENT DOCUMENTS 6,649,647 B1 11/2003 Haynes et al. ............. 514/450
2005/0119232 A1 6/2005 Haynes ..................... 514/100

FOREIGN PATENT DOCUMENTS

WO 00/04024 1/2000

OTHER PUBLICATIONS

Johnson J L; Werbel L M: "Synthesis and antileishmanial activity of 6-methoxy-4-methyl-N-'6-(substituted-1-piperazinyl)hexyl!-8-quinolina mines and related compounds" Journal of Medicinal Chemistry, Bd. 26, Nr. 2, 1983, Seiten 185-194, XP002347850.

*Primary Examiner*—J. Parsa
(74) *Attorney, Agent, or Firm*—Michael A. Miller

(57) ABSTRACT

A novel one-stage process for preparing 10α-[4'-(S,S-dioxothiomorpholin-1'-yl)]-10-deoxo-10-dihydroartemisinin (1a) by reacting a compound of the formula (1b)

(1b)

in which X is a halogen atom with thiomorpholine dioxide at a temperature in the range of −30° C. to +20° C. is provided.

25 Claims, No Drawings

PROCESS FOR PREPARING 10α-[4'-(S,S-DIOXOTHIOMORPHOLIN-1'-YL)]-10-DEOXO-10-DIHYDROARTEMISININ

FIELD OF THE INVENTION

The invention relates to a novel, improved process for preparing 10α-[4'-(S,S-di-oxothiomorpholin-1'-yl)]-10-deoxo-10-dihydroartemisinin.

BACKGROUND OF THE INVENTION

WO-A-03/076446 discloses a multitude of C-10-substituted derivatives of dihydroartemisinin of the following formula

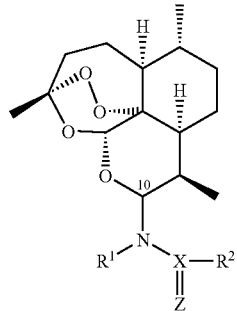

in which $R^1$ and $R^2$ may be a wide variety of organic radicals optionally containing heteroatom moieties, X is, for example, S, an S(=O), $PR^3$, P—O—$R^3$ or P—N($R^4$)—$R^3$ group, with $R^3$ and $R^4$ being in turn organic radicals, and Z is oxygen, sulphur or an $NR^5$ radical, with $R^5$ being in turn an organic radical.

WO-A-00/04024 discloses further C-10-substituted derivatives of dihydroartemisinin of the general formula (1)

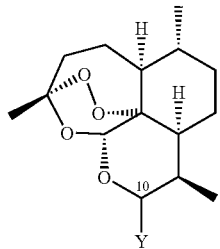

where Y is a halogen atom, an optionally substituted cycloalkyl, aryl, a C-bonded heteroaryl or a heterocycloalkyl radical, or is an $NR^1R^2$ group where $R^1$ is hydrogen or an optionally substituted alkyl, alkenyl or alkynyl radical and $R^2$ is an optionally substituted alkyl, alkenyl, alkynyl, cycloalkyl, aryl or aralkyl radical, or else $R^1$ and $R^2$ together with the adjacent nitrogen atom are an optionally substituted heterocyclic group or an amino group derived from an optionally substituted amino acid ester.

Such compounds described in WO-A-03/076446 and WO-A-00/04024 are effective in the treatment of parasitic infections such as malaria, neosporosis or coccidiosis.

Also mentioned in WO-A-00/04024 is 10α-[4'-(S,S-di-oxothiomorpholin-1'-yl)]-10-deoxo-10-dihydroartemisinin (1a) as a compound of the general formula (1).

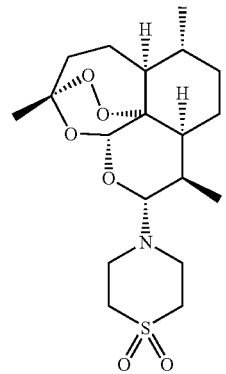

WO-A-00/04024 describes the synthesis of the compounds of the general formula (1) by reacting a dihydroartemisinin of the formula (2)

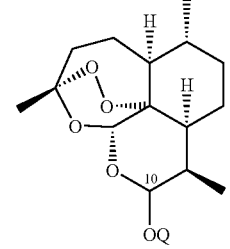

where Q is a hydrogen atom or a trimethylsilyl group with a halogenating agent to form a compound of the formula (1) in which Y is a halogen atom, and subsequently reacting with a Grignard of the formula YMgX where X=halogen or with an amine of the general formula $HNR^1R^2$.

The preparation of 10α-[4'-(S,S-dioxothiomorpholin-1'-yl)]-10-deoxo-10-dihydroartemisinin (1a) is described in WO-A-00/04024 starting from dihydroartemisinin of the formula (2a) and thiomorpholine of the formula (3). According to Examples 3(a), 3(b), 6 and 7, dihydroartemisinin (2a) is reacted first with chlorotrimethylsilane and then with bromotrimethylsilane, and then 3 equivalents of thiomorpholine are added to form the compound of the formula (4). This compound of the formula (4) is isolated as an intermediate. Both reactions are effected at very low temperatures in the region of 0° C. and room temperature. The subsequent oxidation of the compound of the formula (4) affords the target compound of the formula (1a), NMO meaning 4-methylmorpholine N-oxide and TPAP=tetrapropylammonium perruthenate.

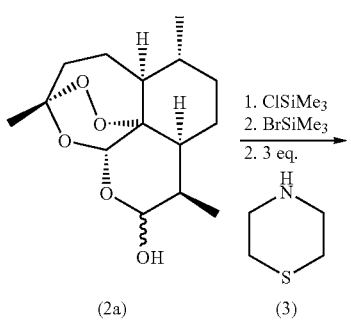

-continued

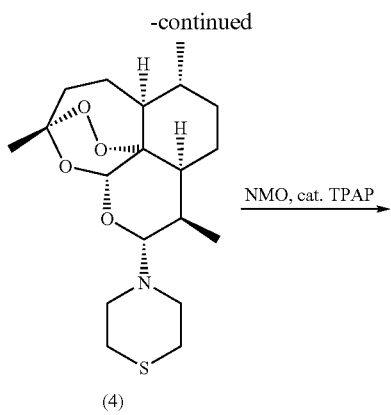

(4)

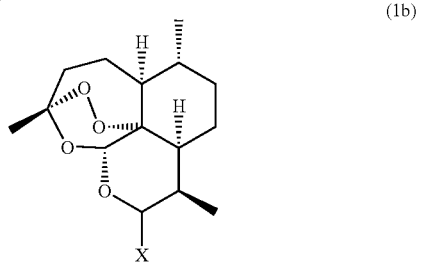

(1a)

A disadvantage of this synthesis is that it is a two-stage process and 3 equivalents of the expensive thiomorpholine feedstock have to be used.

It is thus an object of the present invention to provide an improved process for preparing 10α-[4'-(S,S-dioxothiomorpholin-1'-yl)]-10-deoxo-10-dihydroartemisinin (1a).

SUMMARY OF THE INVENTION

Surprisingly, it is possible to prepare 10α-[4'-(S,S-dioxothiomorpholin-1'-yl)]-10-deoxo-10-dihydroartemisinin (1a) in a one-stage process from 10-halo-10-deoxo-10-dihydroartemisinin (1b) and thiomorpholine oxide (3).

The invention provides a process for preparing 10α-[4'-(S,S-dioxothiomorpholin-1'-yl)]-10-deoxo-10-dihydroartemisinin (1a), which is characterized in that a compound of the formula (1b)

(1b)

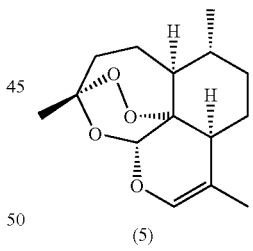

in which X is a halogen atom is reacted with thiomorpholine dioxide of the formula (3)

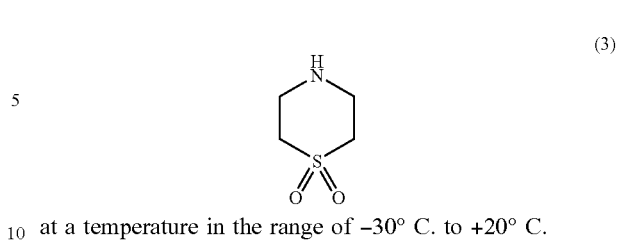

at a temperature in the range of −30° C. to +20° C.

DESCRIPTION OF THE INVENTION

This process has one stage. Its successful performability is surprising in several ways: It is known that thiomorpholine dioxide is a distinctly poorer nucleophile than thiomorpholine owing to the electron-withdrawing effect of the sulphone group. Thus, nucleophilic substitution reactions using thiomorpholine dioxide need distinctly higher reaction temperatures than when thiomorpholine is used (see, for example, J. L. Johnson, L. M. Werbel, J. Med. Chem. 1983, 26, 185-194). At the same time, though, it is sufficiently well known from the literature that dihydroartemisinin of the formula (2) and structurally related compounds decompose in the course of heating owing to the thermal stability of the peroxo group (see, for example, A. J. Lin, A. D. Theohanrides, D. L. Klayman, Tetrahedron 1986, 42 (8), 2181-4; X. D. Luo, H. J. C. Yeh, A. Brossi, J. L. Flippen-Anderson, R. Gilardi, Heterocycles 1985, 23 (4), 881-7). The removal of decomposition products formed in this way from the desired product is difficult owing to the structural similarity. High reaction temperatures should therefore be avoided in order to prevent the formation of decomposition products. This would cause longer reaction times.

In the case of longer reaction times at lower temperatures, though, the increased formation of by-products such as the compounds of the formula (5) and (6) is to be expected, which have already been described in the literature (see R. K. Haynes, H. Chan, M. Cheung, S. T. Chung, W. Lam, H. Tsang, A. Voerste, I. D. Williams, Eur. J. Org. Chem. 2003, 2098-2114).

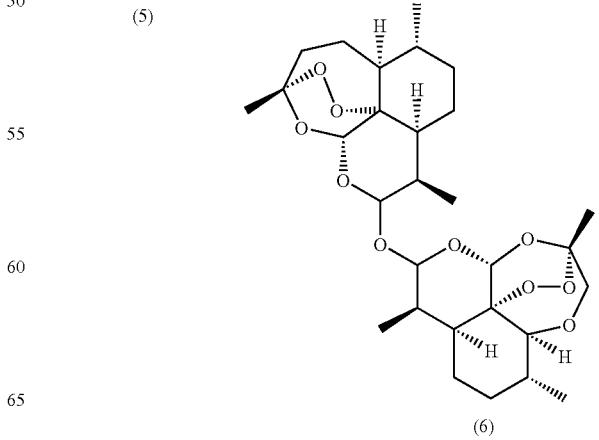

It is thus surprising that the reaction of the dihydroartemisinin derivate of the formula (1b) with thiomorpholine dioxide of the formula (3) takes place at low temperatures without significant formation of by-products.

Thiomorpholine dioxide is a commercially available reagent.

In the process according to the invention, the reactant used is a compound of the formula (1b) where X is a halogen atom, preferably chlorine or bromine, in particular chlorine.

This compound of the formula (1b) may be formed in situ beforehand according to WO-A-00/04024 and does not have to be isolated. For the purpose of the preparation, dihydroartemisinin of the formula (2) can be reacted with a halogenating agent. Suitable halogenating agents are diethylaminosulphur trifluoride, chlorotrimethylsilane, bromotrimethylsilane, iodotrimethylsilane, HCl, HBr or HI.

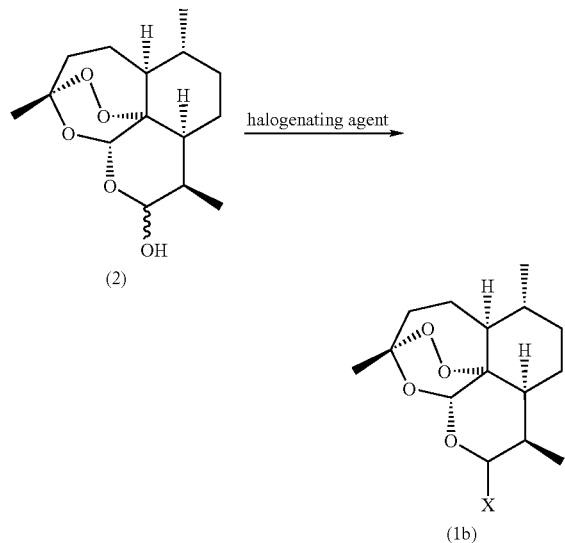

Dihydroartemisinin of the formula (2) is reacted more preferably with HBr gas or particularly preferably HCl gas in the presence of $CaCl_2$. HBr and HCl gas are inexpensive and readily available reagents.

Alternatively, as likewise described in WO-A-00/04024, the starting material, instead of the dihydroartemisinin of the formula (2), can also be the derivative trimethylsilyl-protected correspondingly in the 10-position and this can be reacted with the halogenating agent.

To improve the yield and avoid by-products, it is advantageous to remove water formed in this reaction. This is suitably effected by using molecular sieve or desiccants such as $MgCl_2$, $CaCl_2$, LiCl, $Na_2SO_4$, $MgSO_4$ or $CaSO_4$. It has been found to be useful to use 1-20 equivalents, preferably 1-5 equivalents, more preferably 2-3 equivalents, of the desiccant.

The in-situ formation of compound (1b) is carried out at a temperature in the range of –30° C. to +20° C., preferably in the range of –20° C. to +10° C. and in particular in the range of –10° C. to 0° C.

It has been found to be useful to carry out this reaction in polar non-nucleophilic solvents, preferably in halogenated aliphatic or aromatic hydrocarbons, in particular chlorinated aliphatic or aromatic hydrocarbons. It is possible, for example, to use chlorobenzene. Particular preference is given to methylene chloride.

In the inventive reaction of the compound of the formula (1b) formed in situ with thiomorpholine dioxide, typically 1-3 equivalents of thiomorpholine dioxide are used. However, the reaction advantageously also proceeds with distinctly smaller amounts than 3 equivalents of thiomorpholine. Preference is given to using 1-2.5, more preferably 1-2.2 and in particular 2, equivalents of thiomorpholine dioxide. This leads to an optimal suppression of side reactions.

The inventive reaction of the compound of the formula (1b) is carried out at a temperature in the range of –30° C. to +20° C., preferably in the range of –20° C. to +10° C. and in particular in the range of –10° C. to 0° C.

Typically, this reaction is carried out in the same solvent as in the in-situ preparation of the starting material of the formula (1b).

It has been found to be useful to work in the presence of an auxiliary base which is more strongly basic than thiomorpholine dioxide in order to scavenge the HX where X=halogen, preferably chlorine or bromine, formed in the reaction of the compound of the formula (1b) with thiomorpholine dioxide. This measure allows a minimization of the amount of thiomorpholine dioxide. Typically, 1 equivalent of the auxiliary base is used. Preference is given to using amines such as pyridine or triethylamine. Particular preference is given to triethylamine. It is found that, surprisingly, when this auxiliary base is used, there is no increased formation of the elimination product of the formula (5).

The process according to the invention is typically carried out in such a way that a solution of the thiomorpholine dioxide and of the auxiliary base in a solvent which is preferably identical to the solvent in which the compound (1b) is dissolved is added at the above-specified reaction temperature to the solution of the compound of the general formula (1b) generated in situ. After suitable continued stirring, the phases are separated. From the organic phase, the desired 10α-[4'-(S,S-dioxothiomorpholin-1'-yl)]-10-deoxo-10-dihydroartemisinin (1a) product may be obtained by customary workup methods such as distillation and recrystallization. The recrystallization is preferably carried out from an alcohol, more preferably from methanol, ethanol, butanol or in particular isopropanol.

It is also possible via the process according to the invention to obtain salts of 10α-[4'-(S,S-dioxothiomorpholin-1'-yl)]-10-deoxo-10-dihydroartemisinin (1a). This includes any salts which can be obtained by reaction of the compound (1a) with a suitable organic or inorganic acid. Preferred salts are obtained by reaction of a mineral acid such HCl or HBr with protonation of the nitrogen.

EXAMPLE 1

Preparation of 10α-[4'-(S,S-dioxothiomorpholin-1'-yl)]-10-deoxo-10-dihydroartemisinin (1a)

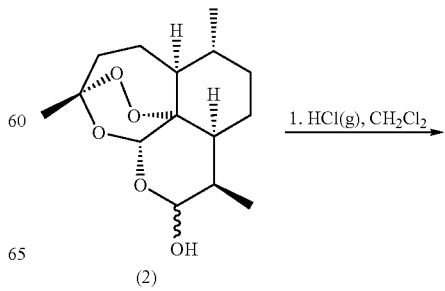

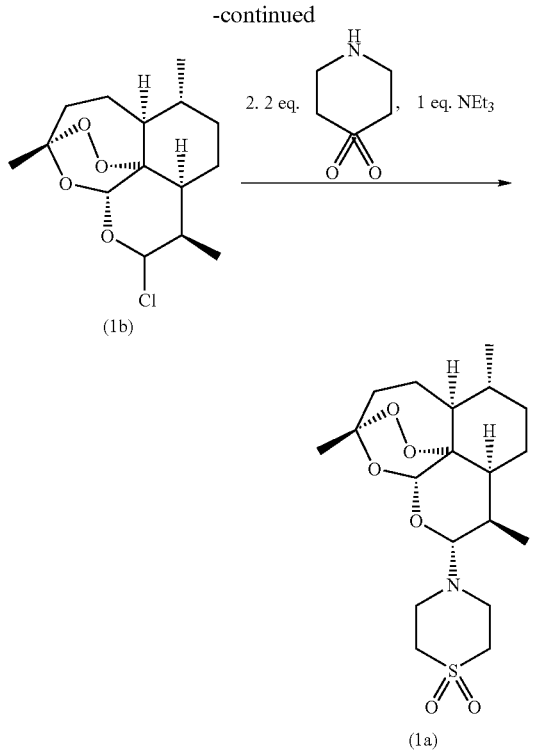

Approx. 26 g of HCl gas (722 mmol) were introduced at −10° C. within 70 min into a suspension of 60 g of compound of the formula (1b) (having a content of 98.4% by weight, corresponding to 211 mmol) and 37.7 g of CaCl$_2$ powder (366 mmol) in 800 ml of CH$_2$Cl$_2$.

The reaction proceeded initially exothermically, so that the internal temperature rose to −4° C. with jacket cooling of −10° C. HCl gas was introduced until penetration could be seen at the bubble counter. The mixture was left to stir for a further 15 min and a nitrogen stream was subsequently passed through the reaction vessel for 85 min in order to displace the excess HCl gas.

Subsequently, at a temperature of −5 to −10° C. within 50 min, a solution of 56.9 g of thiomorpholine dioxide (having a content of 98% by weight, corresponding to 422 mmol) and 23.5 g of triethylamine (having a content of 98% by weight, corresponding to 232 mmol) were added to 200 ml of CH$_2$Cl$_2$.

After the mixture had been stirred at a temperature of −5° C. for a further 2 h, 500 ml of water were added at +6° C. After warming to RT, the organic phase (lower) was removed and the aqueous phase was extracted twice with 100 ml each time of CH$_2$Cl$_2$. The solvent of the combined organic phases was removed under reduced pressure. Subsequently, 435 g of isopropanol were added and the residue was dissolved at 50° C. The mixture was cooled to 20° C. within one hour and stirred at this temperature for a further 3 hours. The solid was subsequently filtered off (33.1 g) and dissolved again at 60° C. in 248.4 g of isopropanol. After cooling to 20° C. within 1 hour and stirring at 20° C. for a further 3 hours, the colourless solid was filtered off. 27.4 g (32.1%) of 10α-[4'-(S,S-dioxothiomorpholin-1'-yl)]-10-deoxo-10-dihydroartemisinin (artemisone) were obtained (100% by weight by HPLC analysis).

$^1$H NMR (400 MHz, CDCl$_3$): δ=5.26 (s, 1H), 4.20 (d, J=10.3 Hz, 1H), 3.46-3.18 (m, 8H), 2.62-2.54 (m, 1H), 2.36-2.28 (m, 1H), 2.02-1.20 (m, 9H), 1.35 (s, 3H), 1.06-0.92 (m, 1H), 0.93 (d, J=6.0 Hz, 3H), 0.78 (d, J=7.1 Hz, 3H).

What is claimed is:

1. A process for preparing 10.alpha.-[4'-(S,S-dioxothiomorpholin-1'-yl)]-1-0-deoxo-10-dihydroartemisinin (1a), comprising reacting a compound of the formula (1b)

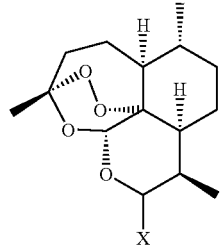

wherein X is a halogen atom
with thiomorpholine dioxide of the formula (3)

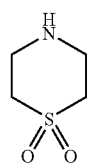

at a temperature in the range of −30° C. to +20° C.

2. The process of claim 1, wherein a compound of the formula (1b) in which X is chlorine or bromine is used.

3. The process of claim 1, wherein the compound of the formula (1b) is formed in situ and is not isolated before the reaction according to claim 1 or 2.

4. The process of claim 3, wherein the compound of the formula (1b) is obtained by reacting a compound of the formula (2)

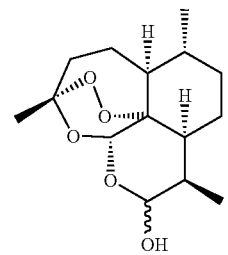

with gaseous HX in which X is bromine or chlorine.

5. The process of claim 4, wherein the reaction of the compound of the formula (2) with gaseous HX is carried out in the presence of molecular sieve or a desiccant.

6. The process of claim 4, wherein the reaction of the compound of the formula (2) is carried out at a temperature in the range of −30° C. to +20° C.

7. The process of claim 1, wherein 1-3 equivalents of thiomorpholine dioxide are used.

8. The process of claim 1, wherein the reaction of the compound of the formula (1b) with thiomorpholine dioxide of the formula (3) is carried out in the presence of an auxiliary base which is more strongly basic than thiomorpholine dioxide.

9. The process of claim 5, wherein the molecular sieve or the desiccant is selected from the group consisting of MgCl$_2$, CaCl$_2$, LiCl, Na$_2$SO$_4$, MgSO$_4$ or CaSO$_4$.

10. The process of claim 6, wherein the temperature is in the range of −20° C. to +10° C.

11. The process of claim 6, wherein the temperature is in the range of −10° C. to 0° C.

12. The process of claim 7, wherein 1 to 2.5 equivalents of thiomorpholine dioxide are used.

13. The process of claim 7, wherein 1 to 2.2 equivalents of thiomorpholine dioxide are used.

14. The process of claim 7, wherein 1 to 2 equivalents of thiomorpholine dioxide are used.

15. The process of claim 8, wherein the reaction is carried out in the presence of an auxiliary based selected from pyridine and triethylamine.

16. A process for preparing 10.alpha-[4'-(S,S-dioxothiomorpholin-1'-yl)]-1-0-deoxo-10-dihydroartemisinin (1a), comprising reacting a compound of the formula (1b)

(1b)

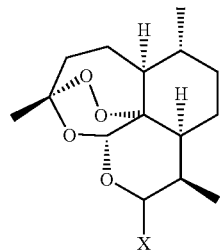

wherein X is a halogen atom
with thiomorpholine dioxide of the formula (3)

(3)

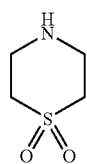

at a temperature in the range of −30° C. to +20° C., and in the presence of an auxiliary base which is more strongly basic than thiomorpholine dioxide.

17. The process of claim 16, wherein a compound of the formula (1b) in which X is chlorine or bromine is used.

18. The process of claim 16, wherein the compound of the formula (1b) is formed in situ and is not isolated before the reaction according to claim 1 or 2.

19. The process of claim 18, wherein the compound of the formula (1b) is obtained by reacting a compound of the formula (2)

(2)

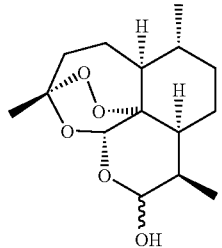

with gaseous HX in which X is bromine or chlorine.

20. The process of claim 19, wherein the reaction of the compound of the formula (2) with gaseous HX is carried out in the presence of molecular sieve or a desiccant.

21. The process of claim 19, wherein the reaction of the compound of the formula (2) is carried out at a temperature in the range of −30° C. to +20° C.

22. The process of claim 16, wherein 1-3 equivalents of thiomorpholine dioxide are used.

23. The process of claim 22, wherein 1 to 2.5 equivalents of thiomorpholine dioxide are used.

24. The process of claim 22, wherein 1 to 2.2 equivalents of thiomorpholine dioxide are used.

25. The process of claim 22, wherein 1 to 2 equivalents of thiomorpholine dioxide are used.

* * * * *